United States Patent [19]

Isbister et al.

[11] Patent Number: 4,562,156
[45] Date of Patent: Dec. 31, 1985

[54] MUTANT MICROORGANISM AND ITS USE IN REMOVING ORGANIC SULFUR COMPOUNDS

[75] Inventors: Jenefir D. Isbister, Potomac, Md.; Richard C. Doyle, Fairfax, Va.

[73] Assignee: Atlantic Research Corporation, Alexandria, Va.

[21] Appl. No.: 512,857

[22] Filed: Jul. 11, 1983

[51] Int. Cl.$^4$ ............................................... C12N 1/20
[52] U.S. Cl. .................................... 435/253; 435/170; 435/251; 435/282; 435/874; 44/1 SR
[58] Field of Search ............... 435/874, 130, 170, 245, 435/251, 253, 282, 262, 41, 877; 44/1 SR

[56] References Cited

U.S. PATENT DOCUMENTS

| | | | |
|---|---|---|---|
| 2,641,564 | 7/1953 | Zobell | 435/282 |
| 4,206,288 | 7/1980 | Detz et al. | 44/1 SR |
| 4,256,485 | 3/1981 | Richardson | 44/1 SR |
| 4,447,539 | 5/1984 | Pillis et al. | 435/877 |

OTHER PUBLICATIONS

Chemical Abstracts, 1981, vol. 94, No. 142230q, Eckart et al, Mikrobol. Landwirtsch., Technal. Umwellschutzes 1980, 135(8) pp. 674–681.
Hartdegen et al, Chemical Engineering Progress, vol. 80, No. 5, May 1984, pp. 63–67.
Eckart et al, Chemical Abstracts, vol. 97, 1982, No. 147259c.
Chemical Abstracts, vol. 78, 1973, No. 94605m.
Chemical Abstracts, vol. 85, 1976, No. 156414d.
Chemical Abstracts, vol. 83, 1975, No. 82530y.
Chemical Abstracts, vol. 84, 1976, No. 46982j.
Chemical Abstracts, vol. 85, 1976, No. 145448s.

Primary Examiner—Christine M. Nucker
Assistant Examiner—William J. Herald
Attorney, Agent, or Firm—Quaintance, Murphy & Presta

[57] ABSTRACT

A novel mutant microorganism Pseudomonas sp. CB1 having a registry number ATCC 39381 has been produced by chemical mutagenesis and is effective in removing organic sulfur compounds from carbonaceous materials such as fossil fuels e.g., coal, petroleum and petroleum products.

4 Claims, No Drawings

MUTANT MICROORGANISM AND ITS USE IN REMOVING ORGANIC SULFUR COMPOUNDS

BACKGROUND

Many grades of coal and petroleum contain large quantities of sulfur compounds which form corrosive air and water pollutant products during combustion. A number of chemical and physical processes have been developed to remove inorganic sulfur contaminants, such as sulfates and iron pyrites. Some organic sulfur compounds, such as mercaptans, aliphatic sulfides and disulfides are relatively amenable to chemical removal. However, the aromatic sulfur compounds, such as diphenylsulfide, benzothiophene, dibenzothiophene and the like, are found in predominating concentrations in coal. These sulfur compounds are resistant to chemical and microbial attack and are frequently characterized as refractory organosulfur compounds.

A number of chemical processes for removal of organic sulfur are under investigation. Among the processes being evaluated on a laboratory or pilot scale are oxydesulfurization, chlorinolysis, oxidation, hydrodesulfurization and Gravimelt. According to Berry [Berry, R. I. (1981), "Guide to Coal-Cleaning Methods," *Chemical Engineering*, January 26], projected total product costs from bench and pilot scale operations ranged from $41 to $58 per ton (in 1979 dollars) for 10 to 50% organic sulfur removal.

Removal of such refractory organic sulfur compounds by microbial treatment would have many important advantages. Since high temperature, high pressure or corrosion resistant equipment are not required for the biological process, inexpensive construction materials can be used leading to low capital costs. Processing costs can also be low if waste materials are utilized to support the microbial growth. Biological treatment can be carried out under ambient conditions in many locales. Microbial treatment is not likely to significantly alter the structure and composition of the coal or to substantially reduce the BTU value of the coal.

Microbiological treatment of petroleum and coal has been under experimental investigation utilizing a variety of microorganisms, including genera such as Pseudomonas, Alcaligenes, Bacillus, Desulfovibrio, Thiobacillus, Arthrobacter, Flavobacterium, Beijerinckia, Rhizobium, and Acinetobacter. Some of these microorganisms showed potential for degrading refractory organic sulfur compounds as discussed by Hedrick et al. [Hedrick et al (1982), "Desulfurization of Coal by Biological Pretreatment," State-of-the-Art]. This article provides a comprehensive summary of such experimental efforts. However, neither this report nor other available art discloses the mutant microorganism Pseudomonas sp. CB1 (ATCC #39381) or its efficacy in removing sulfur from refractory organic sulfur compounds, such as the thiophenes found in carbonaceous materials.

SUMMARY

Pseudomonas sp. CB1, ATCC #39381, is a nonmotile, grame negative rod approximately 0.5 by 1 micron in size, occurring singly or in short chains. It grows aerobically; produces a yellow-green water soluble pigment; is catalase and oxidase positive; does not utilize citrate as a sole carbon source; does not grow at 41° C.; and grows on MacConkey's agar. Colonies formed on nutrient agar are round, flat, opaque and produce a yellow-green pigment. Colonies formed on MacConkey's agar are round, regular and white. This organism does not use naphthalene, phenol or resorcinol as a sole source of carbon for growth and energy. However, the organism is able to use benzoate as a sole carbon source. The organism contains a large ($\geq 25$ megadaltons) plasmid. A culture of this microorganism has been deposited in ATCC and has received the number 39381.

The organism was developed by adaptation of natural organisms to dibenzothiopene (DBT) and selection of the adapted culture for those organisms able to use benzoate as a sole carbon source followed by selection for organisms capable of oxidizing DBT in an aqueous medium. Organisms capable of oxidizing DBT in an aqueous medium were treated by a mutagen to increase DBT oxidation capability.

The new mutant microorganism, CB1 (ATCC #39381), successfully degrades refractory aromatic and aliphatic organic sulfur compounds and is especially useful in oxidizing and removing these contaminants from carbonaceous substrates such as coal, petroleum and petroleum products without utilazation of the carbonaceous material.

The new CB1 microorganism can be used to remove organic sulfur from different grades of coal of various particle sizes from fine to coarse. It can also be used to remove organic sulfur compounds in coal/water fuel slurries and in pipeline slurries.

DETAILED DESCRIPTION

Isolation

Soil samples were obtained in Maryland, Virginia, and from a Pennsylvania coal mine. Microbial populations were isolated from each sample by extraction with modified Ringer's solution, a sterile salts solution containing sodium chloride (0.7%), $CaCl_2$ (0.0026%), KCl (0.035%), and distilled water. Each of the salts extracts containing the microorganisms was placed on nutrient agar and inoculated into Trypticase Soy Broth (TSB) for growth of the cultures. A pure culture of *Pseudomonas putida* was also inoculated into Trypticase Soy Broth.

Adaptation

All of the above microbial cultures were individually adapted to the presence of DBT in Trypticase Soy Broth, and then to the presence of DBT in minimal salts medium (0.02% $MgSO_4$, 0.02% citric acid.$H_2O$, 1.0% $K_2HPO_4$, 0.35% $Na(NH_4)HPO_4$, pH 7). The concentration of the DBT ranged from 100 to 1000 mg/L.

Selection

All of the cultures which had successfully adapted to the presence of DBT (Maryland, Virginia and Pennsylvania soil populations and the *Ps. putida* pure culture) were selected for utilization of benzoate as a carbon source by inoculation into minimal salts medium (no citrate) containing only benzoate (sodium benzoate 0.25%) as the sole carbon source.

All cultures able to use benzoate as a sole carbon source were grown in minimal salts medium containing 0.25% benzoate on a shaking table at room temperature overnight. To evaluate the cultures for oxidation of DBT in aqueous medium, each overnight culture was inoculated with DBT to a final concentration of 200 or 400 mg/L. Media controls were also inoculated with DBT at the same DBT concentrations. After DBT inoculated, the cultures were returned to the shaking table and incubated for several days. To determine the amount of DBT remaining in the aqueous medium, the entire contents of each flask were extracted with methylene chloride. Three of the cultures tested (the Maryland and Virginia soil population and the pure culture of Ps. putida) showed small decreases in solvent extractable DBT concentration. These cultures were maintained separately and as a combination of the three cultures. This combined culture was designated "Combo."

The three individual cultures and "Combo" were further adapted to the presence of DBT and selected for their ability to use benzoate as a sole carbon source.

Mutagen Treatment

Each of these four cultures and the Pennsylvania coal mine cultures were subjected to diethyl sulfate (DES) mutagenesis as described by Roth [Roth, J. R. (1971), "Genetic Techniques in Studies of Bacterial Metabolism: In *Methods in Enzymology*, XVII. A, p. 3–35]. Some of the microorganisms in each of the five cultures survived the DES treatment and were "rescued" by serial dilution (1/100) into fresh nutrient broth for overnight quiescent growth at 35° C.

The microbial cultures resulting from "rescue" in nutrient broth following DES mutgenesis were inoculated into minimal salts medium containing benzoate as a carbon source and grown overnight on a shaking table at room temperature. The culture flask and media control flasks were each inoculated with DBT at varying concentrations (e.g. 100 mg/L, 200 mg/L). The flasks were returned to the shaking table and incubated for varying periods of time (e.g. 18 hours, 4 days, 7 days) prior to extraction of the entire contents of the flask with methylene chloride for DBT analyses. The "Combo" culture was the only one which showed a significant decrease in solvent extractable DBT.

The "Combo" culture following the DES treatment was subcultured into minimal salts medium containing benzoate. This subculture was streaked for isolation onto nutrient agar plates. Single colony isolation was performed three times and from the third isolation, a single colony was subcultured into minimal salts medium plus benzoate and evaluated for DBT oxidation. This triple single colony isolate was designated CB1 and identified as a Pseudomonas sp.

Plasmid Analysis

A variety of chemical agents, such as acridine orange, as well as growth at elevated temperatures are able to free or "cure" some bacterial cells of plasmid DNA molecules. Plsmids which exist as autonomously replicating circular DNA duplexes are eliminated by these agents either because of interference with replication (acridines) or by alteration of their membrane attachment sites (elevated temperatures).

The curing procedure used with CB1 was performed in accordance with the one disclosed in the "Manual of Methods for General Bacteriology" [Gerhardt, P. (1981), *Manual of Methods for General Bacteriology*, American Society for Microbiology, Washington, D.C.]. The CB1 culture in the logarithmic growth phase was inoculated at $10^3$ to $10^4$ cells into a series of tubes containing nutrient broth with 50 or 250 mg/L acridine organe. Cultures were incubated overnight with aeration at 25° C. or at 40° C. A portion of each culture was then diluted 1:100 into fresh medium and allowed to grow at 25° C. or 40° C. with no aeration. Appropriate dilutions of the culture were placed on nutrient agar to obtain single colonies. Single colony isolates were tested for DBT oxidation.

Stock cultures of CB1 (ATCC #39381), Ps. putida and two acridine orange treated single colony isolates which showed decreased DBT oxidation, were streaked onto nutrient agar plates and treated for isolation of plasmid DNA using the methods of Birnboim and Doly [Birnboim, H. C. and Doly, J., "A Rapid Alkaline Extraction Procedure for Screening Recombinant Plasmid DNA," Nucleic Acids Research, 7:1513–1523] and "lysis in the well" techniques of Newland et at. [Newland, J. W. et al. (1980), "Rapid Screening for Plasmids in Environmental Isolates of *Vibrio cholerae* by an "in the well" Lysis Technique Using Horizontal Gel Electrophoresis," Abstracts Proc., 3rd Annual Mid-Atlantic Regional Extrachromosomal Elements Meeting, Plasmid, 3:238].

These plasmid analytic procedures demonstrated that "uncured" CB1 (ATCC #39381) contained a large plasmid $\geq 25$ megadaltons in size. Untreated Ps. putida, one of the parent strains in the original combination culture, did not contain any plasmids detectable by these procedures. A treated CB1 isolate, which no longer oxidized DBT following acridine orange treatment, was also analyzed and found to contain a large plasmid similar in molecular weight to the plasmid found in CB1. In this case, the acridine orange treatment apparently affected the microbial genetic material without eliminating the plasmid. The foregoing results indicated that oxidation of DBT by CB1 is not plasmid mediated.

Biochemical Characterization

Biochemical characterizations of CB1, stock cultures of Ps. aeruginosa, Ps. putida and Ps. stutzeri were performed using the API 20E System [API 20E System Analytical Profile Index, Analab Products, Plainview, NY]. Profiles for CB1 and the closely related Pseudomonas species are presented in Table 1. It will be noted that important differences between CB1 and each of the other Pseudomonads are demonstrated.

Mechanistic Studies With DBT

Radioisotope studies in which CB1 was incubated with $^{14}$C-DBT and $^{35}$S-DBT indicated that the DBT sulfur and carbon skeleton were oxidized to water soluble compounds. However, no $^{14}CO_2$ was produced indicating that CB1 did not utilize the DBT carbon skeleton as a carbon source. The biomass was removed by centrifugation and filtration through a 0.2 micron filter. The filtrate was analyzed for sulfate as described in the Hach Handbook for Water Analysis [Hach Chemical Company, 1979] and by ion chromatography. The two analytical methods gave comparable results. Sulfate concentrations in the CB1 treated DBT medium were 100 and 99 mg/L. Sulfate concentrations in the controls were 55 and 67 mg/L. These data indicate that CB1 acts on DBT by oxidation of the sulfur group to produce inorganic sulfate. This mechanism differs from all other literature reports of microbial DBT degradation where the major product is reported to be 3-hydroxy-2-formyl benzothiophene [Kodama, K. et al. (1973), "Identification of Microbial Products from Dibenzothiophene and Its Proposed Oxidation Pathway," Agr. Biol. Chem., 37(1), p. 45–50].

Mechanistic Studies with Coal

Organic sulfur in coal is determined by a round-about method which involves analysis for pyritic sulfur, sulfate sulfur and total sulfur. The organic sulfur is determined by the difference between the total sulfur and the sum of the pyritic sulfur and sulfate sulfur. To prove that CB1 acts only on the organic sulfur in coal, the coal was washed to remove the sulfate sulfur. Decrease in the total sulfur content of the washed coals ranged from 8 to 34% depending on coal type and particle size. To prove that CB1 does not act on pyritic sulfur, the following experiments were performed.

CB1 was incubated with 0.25 g iron pyrite (approximately 325 mesh)/100 mL water on a shaking table at 25° C. A control flask contained only minimal salts medium, benzoate and iron pyrite. Following the incubation, the contents of each flask were centrifuged and the supernatant removed and filtered through a 0.2 micron filter. The filtered supernatant was analyzed for sulfate using the method described in the Hach Handbook for Water Analysis [Hach Chemical Company, 1979]. The pyrite/biomass harvested from the centrifugation was dried at 60° C. overnight and analyzed for total sulfur content using a Fisher total sulfur analyzer. The total sulfur contents of the control and experimental pyrite (treated with CB1) were identical. These results indicate that CB1 does not oxidize iron pyrite. Therefore, it can be concluded that only the organic sulfur forms in coal are oxidized by CB1.

TABLE 1

| API Test | API 20 E SYSTEM TEST Organism | | | |
|---|---|---|---|---|
| | Ps. aeroginosa | Ps. putida | CB1 | Ps. stutzeri |
| ONPG | − | − | − | − |
| ADH | + | + | − | − |
| LDC | − | − | − | − |
| LDC | − | − | − | − |
| ODC | − | − | − | − |
| CIT | + | − | − | − |
| HS | − | − | − | − |
| URE | + | + | − | − |
| TDA | − | − | − | − |
| IND | − | − | − | − |
| VP | − | − | − | − |
| GEL | + | − | − | − |
| GLU | | − | − | − |
| man | − | − | − | − |
| ino | − | − | − | − |
| sor | − | − | − | − |
| rha | − | − | − | − |
| sac | | − | − | − |
| mel | − | − | − | − |
| amy | − | − | − | − |
| ara | − | − | − | − |
| oxi | + | + | + | + |
| NO | − | − | − | + |
| N gas | | − | − | − |
| Motility | + | + | − | + |
| MAC | + | − | + | − |
| OF-O | + | + | + | + |
| OF-F | − | − | − | − |
| 41 C | + | + | − | + |
| phenol | | | − | |
| resorcinol | | | − | |
| benzoate | | | + | − |

EXAMPLE 1

The oxidation of DBT from aqueous medium by the untreated "Combo" microbial culture and the mutant organism CB1 was evaluated under varying conditions of incubation time, DBT concentration and temperature. Results of these experiments, presented in Tables 2 and 3, demonstrate that CB1 oxidized significantly greater quantities of DBT in the aqueous medium than the untreated parent culture.

EXAMPLE 2

The ability of CB1 to oxidize other organic sulfur compounds in an aqueous medium was evaluated in a series of studies. CB1 cultures were inoculated into minimal salts medium containing benzoate (0.25%) for overnight growth on a shaking table at 25° C. A specified concentration of a selected organic sulfur compound was added to a flask containing an overnight culture of CB1.

TABLE 2

Comparison of the Ability of CB1 and the Parent Culture (Combo) to Oxidize DBT

| Culture | Incubation Time | Initial DBT Conc. mg/L | % Decrease in DBT |
|---|---|---|---|
| Combo | 3 days | 50 | 4 |
| Combo | 5 days | 50 | 3 |
| Combo | 7 days | 100 | 7 |
| Combo | 7 days | 200 | 0 |
| Combo | 10 days | 200 | 10 |
| Combo | 10 days | 100 | 7 |
| CB1 | 18 hours | 100 | 62 |
| CB1 | 18 hours | 100 | 65 |
| CB1 | 18 hours | 100 | 60 |

TABLE 3

The Effect of Concentration and Temperature On DBT Oxidation by CB1

| Incubation Time | Incubation Temperature (°C.) | Initial DBT Conc. mg/L | % Decrease in DBT |
|---|---|---|---|
| 18 hr | 25 | 200 | 71 |
| 72 hr | 25 | 200 | 88 |
| 18 hr | 25 | 250 | 46 |
| 18 hr | 25 | 428 | 67 |
| 18 hr | 25 | 800 | 44 |
| 18 hr | 25 | 800 | 58 |
| 18 hr | 35 | 250 | 83 |
| 18 hr | 35 | 200 | 94 |
| 18 hr | 40 | 200 | 76 |

Flasks containing the microbial culture and the organic sulfur compounds were incubated quiescently for 24–48 hours prior to extraction of the entire contents of the culture flasks for the organic sulfur form. The contents of each flask were extracted three times with 10 mL methylene chloride and the extract was analyzed by gas chromatography. Media control flasks contained minimal salts, benzoate and the specified concentration of the organic sulfur compound to be evaluated. A second set of media control flasks were dosed and extracted immediately to determine the extraction efficiency of each organic sulfur compound. Data presented in Table 4 demonstrate that the mutant microorganism, CB1, removed significant quantities of solvent extractable organic sulfur compounds from aqueous medium.

EXAMPLE 3

Studies were performed to determine the ability of the mutant organism CB1 to remove sulfur from different coal samples and different coal particle sizes. CB1 cultures were inoculated into minimal salts medium containing benzoate (0.25%) for overnight growth on a shaking table at 25° C. Powdered coal was added to each 18–24 hour microbial culture at 5% (w/v). Flasks containing the microbial culture/coal mixture were replaced on the shaking table and incubated for 24–48 hours prior to removal of the coal by centrifugation, washing of the coal with distilled water and analysis of the coal for total sulfur.

It should be noted that results of these experiments are given in terms of total sulfur because no analytical method is currently available to accurately determine the organic sulfur content of coal. Wentz coal and Montcoal were selected for testing with CB1 because organic sulfur forms are reported to make up approximately 90% of the total sulfur content of these coals. Data in Table 5 demonstrate that treatment of the coal samples with the mutant microorganism, CB1, resulted in a significant decrease in the total sulfur content of the coal when the particle size is 250 micron (60 mesh) or less.

EXAMPLE 4

Experiments were performed to evaluate the desulfurization capability of CB1 when used with high sulfur coals. CB1 cultures were inoculated into minimal salts medium containing benzoate (0.25%) for overnight growth on a

TABLE 4

Oxidation of Other Organic Sulfur Compounds by CB1

| Compound | Incubation Time | Initial Conc. mg/L | % Reduction |
|---|---|---|---|
| n-octyl sulfide | 24 h | 100 | 44 |
|  | 24 h | 200 | 85 |
|  | 24 h | 200 | 81 |
| Benzyl methyl sulfide | 24 h | 100 | 31 |
|  | 24 h | 100 | 32 |
| Thioanisole | 24 h | 100 | 45 |
|  | 24 h | 100 | 51 |
| 1-benzothiophene | 24 h | 200 | 81 |

TABLE 5

Coal Desulfurization Studies

| Coal Sample | Particle Size (micron) | Total Sulfur (%) | Organic Sulfur (%) | % Reduction in Total Sulfur |
|---|---|---|---|---|
| Wentz | 245–75 | 0.67 | 0.6 | 16 |
|  |  |  |  | 22 |
| Wentz | 75 | 0.67 | 0.60 | 21.5 |
|  |  |  |  | 25 |
| Montcoal | 245 | 0.80 | 0.72 | 22 |
|  |  |  |  | 21 |
| Montcoal | 80% ≧ 600 micron | 0.80 | 0.72 | — | shaking table at 25° C. Powdered coal was added to each 18 to 24 hour microbial culture at 10% (w/v). Flasks containing the microbial culture/coal mixture were replaced on the shaking table and incubated for 24 hours prior to removal of the coal by centrifugation. Total sulfur analyses were performed on untreated dried coal from each coal sample, on coal samples washed for 24 hours with the minimal salts media (no microorganisms) and on coal samples treated with CB1. Data in Table 6 illustrates organic and total sulfur removal from Sewickeley and Peabody Ill. #6 coal samples by treatment with CB1.

While the present invention has been described by specific embodiments thereof, it should not be limited thereto since obvious modifications will occur to those skilled in the art without departing from the spirit of the invention or the scope of the claims.

TABLE 6

Desulfurization of Sewickeley and Peabody Illinois #6 Coal

| Sample | Total Sulfur (%) | Decrease In Total Sulfur | Decrease in Organic Sulfur |
|---|---|---|---|
| Sewickeley control (325 mesh) | 5.1 |  |  |
| washed | 4.1 |  |  |
| treated | 3.1 | 24% | 53% |
| Sewickeley control (325 mesh) | 4.95 |  |  |
| washed | 4.28 |  |  |
| treated | 3.56 | 17% | 48% |
| Peabody control (−60 mesh) | 3.4 |  |  |
| washed | 3.3 |  |  |
| treated | 2.6 | 21% | 53% |
| Peabody control (−270 mesh) | 3.8 |  |  |
| washed | 3.6 |  |  |
| treated | 2.36 | 34% | 93% |
| APPROXIMATE ANALYSIS (%) |  |  |  |
| Sewickeley coal |  |  |  |
| pyritic sulfur | 2.1 |  |  |
| sulfate sulfur | 1.0 |  |  |
| organic sulfur | 1.9 |  |  |
| total sulfur | 5.0 |  |  |
| Peabody coal |  |  |  |
| pyritic sulfur | 2.07 |  |  |
| sulfate sulfur | 0.5 |  |  |
| organic sulfur | 1.33 |  |  |
| total sulfur | 3.5 |  |  |

We claim:

1. A biologically pure culture of mutant Pseudomonas sp. CB1 ATCC #39381.

2. A process for removing organic sulfur compounds from a carbonaceous substrate comprising treating said substrate with a culture of Pseudomonas sp. CB1 ATCC #39381.

3. The process of claim 2 in which the substrate is coal.

4. The process of claim 2 in which the substrate is petroleum and products thereof.

* * * * *

UNITED STATES PATENT AND TRADEMARK OFFICE
CERTIFICATE OF CORRECTION

PATENT NO. : 4,562,156

DATED : December 31, 1985

INVENTOR(S) : Isbister, Jenefir and Doyle, Richard

It is certified that error appears in the above-identified patent and that said Letters Patent is hereby corrected as shown below:

On the Cover Page, 2nd column, line 1, for "Mikrobol", read --Mikrobiol--; for "Technal", read --Technol--; for "Umwell", read --Umwelt--.

Column 1, Line 62, for "grame", read --gram--.
Column 2, Line 23, for "utilazation", read --utilization--.
Column 2, Line 40, for "placed", read --plated--.
Column 3, Line 2, for "inoculated", read --inoculation--.
Column 3, Line 28, for "mutgenesis", read --mutagenesis--.
Column 3, Line 31, for "flask", read --flasks--.
Column 3, Line 54, for "Plsmids", read --Plasmids,--.
Column 3, Line 55, after "duplexes" and before "are", insert --,--.

Column 5, Line 1, delete the heading "Mechanistic Studies with Coal".

Column 5, please move Line 3 to begin after Table 1 and before Line 35.

Column 5, Table 1, in the first column headed "Test", at the third listed compound, after "ADH" and before "LDC", delete the row "LDC    -    -    -    -".

UNITED STATES PATENT OFFICE
CERTIFICATE OF CORRECTION

Patent No. 4,562,156　　　　　　　　　　Dated December 31, 1985

Inventor(s) Isbister, Jenefir and Doyle, Richard

It is certified that error appears in the above-identified patent and that said Letters Patent are hereby corrected as shown below:

Column 5, Table 1, in the first column headed "Test", at the seventh listed compound, for "HS", read --$H_2S$--.

Column 6, Line 45, after "for 24", delete "-48".
Column 6, Line 53, for "were", read --was--.
Column 6, please move the paragraph delineated by Lines 5-13 to begin after Table 3 and before Line 44.
Column 7, please move Table 4 which appears at Lines 24-35 to Column 7, Line 1.
Column 7, please move Table 5 which appears at Lines 35-49 to Column 7, Line 17, after "less." and before "EXAMPLE 4".

Signed and Sealed this

Twenty-fourth Day of June 1986

[SEAL]

Attest:

Attesting Officer

DONALD J. QUIGG

Commissioner of Patents and Trademarks